(12) United States Patent
Chen

(10) Patent No.: US 6,423,074 B1
(45) Date of Patent: Jul. 23, 2002

(54) FLEXIBLE IRRIGATION/ASPIRATION TIP ASSEMBLY FOR PROVIDING IRRIGATION TO AN EYE CAPSULE AND FOR ASPIRATING FLUID FROM THE EYE CAPSULE

(75) Inventor: Jerry S. J. Chen, Orange, CA (US)

(73) Assignee: Allergan Sales, Inc., Irvine, CA (US)

(*) Notice: Subject to any disclaimer, the term of this patent is extended or adjusted under 35 U.S.C. 154(b) by 0 days.

(21) Appl. No.: 09/470,090

(22) Filed: Dec. 21, 1999

(51) Int. Cl.[7] .................................................. A61F 9/00
(52) U.S. Cl. ...................................................... 606/107
(58) Field of Search .............................. 606/107, 108, 606/166, 170

(56) References Cited

U.S. PATENT DOCUMENTS

| 5,084,009 A | 1/1992 | Mackool | |
|---|---|---|---|
| 5,084,012 A | 1/1992 | Kelman | |
| 5,154,694 A | 10/1992 | Kelman | |
| 5,217,465 A | 6/1993 | Steppe | |
| 5,282,786 A | 2/1994 | Ureche | |
| 5,286,256 A | 2/1994 | Mackool | |
| 5,290,295 A | * 3/1994 | Querals et al. | 606/108 |
| 5,354,265 A | 10/1994 | Mackool | |
| 5,364,405 A | 11/1994 | Zaleski | |
| 5,417,654 A | 5/1995 | Kelman | |
| 5,505,693 A | 4/1996 | Mackool | |
| 5,669,926 A | * 9/1997 | Aust et al. | 606/170 |
| 5,989,209 A | * 11/1999 | Barrett | 606/107 |

FOREIGN PATENT DOCUMENTS

WO    WO9816155    4/1998

* cited by examiner

Primary Examiner—Eduardo C. Robert
(74) Attorney, Agent, or Firm—Walter A. Hackler

(57) ABSTRACT

A flexible tip I/A tip assembly includes an elongated sleeve for protecting an eye capsule wound through which the sleeve is inserted and for containing irrigation fluid. The sleeve includes a lumen therethrough and a nipple for removably coupling the elongated sleeve to a handle by elastomeric contact therewith. A retractor with a worm is disposed within the sleeve for transferring aspiration in any angle of the eye capsule. The sleeve and the retractor are held in operational relationship with the handpiece by a nipple which, due to its transparency, enables visual adjustment, alignment, installation and confirmation of the operative relationship therebetween.

2 Claims, 4 Drawing Sheets

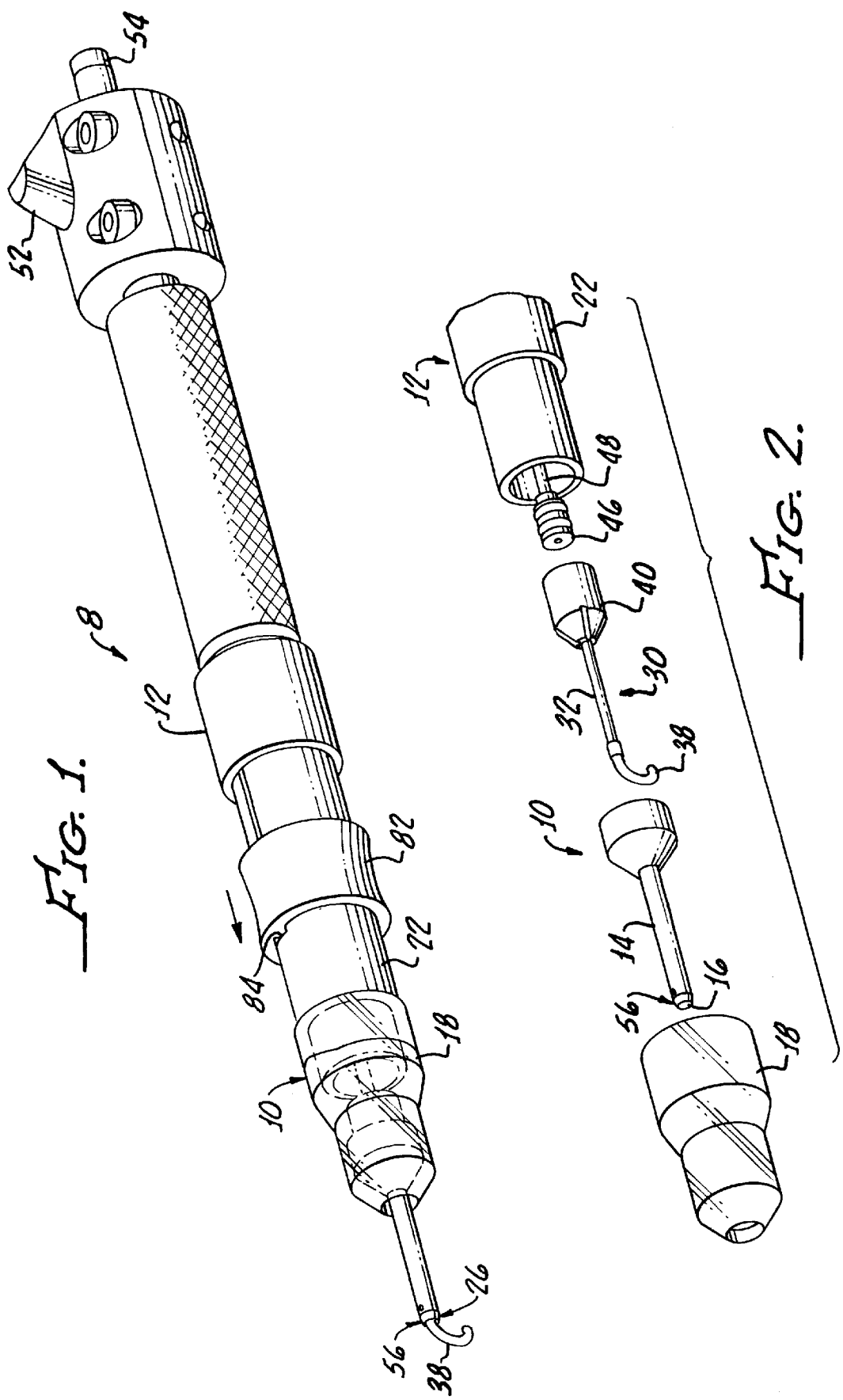

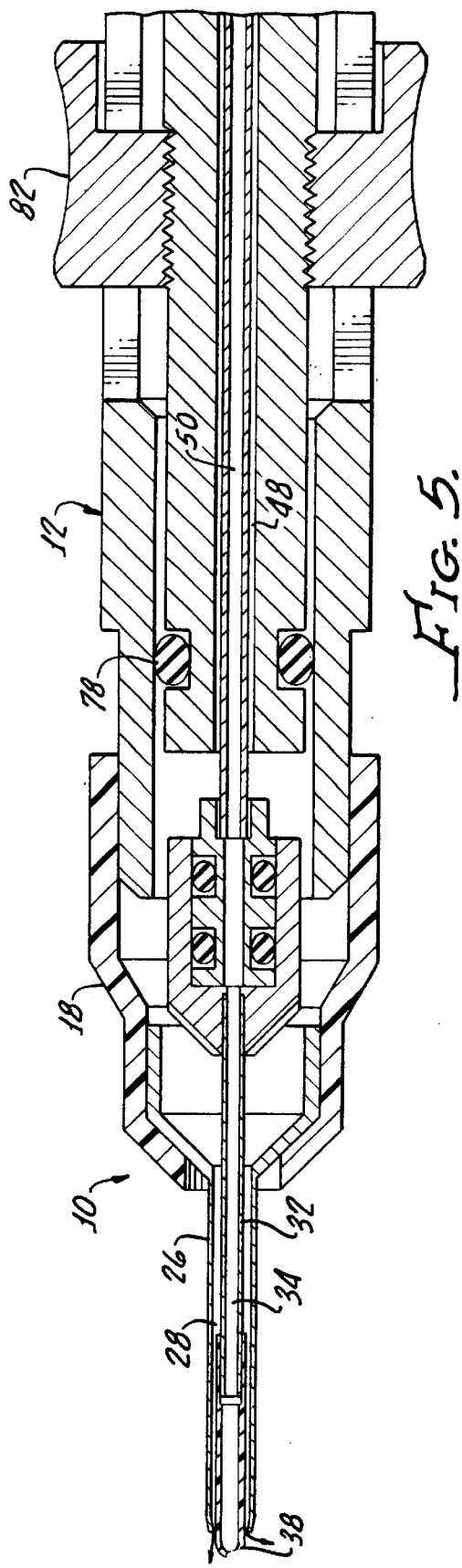
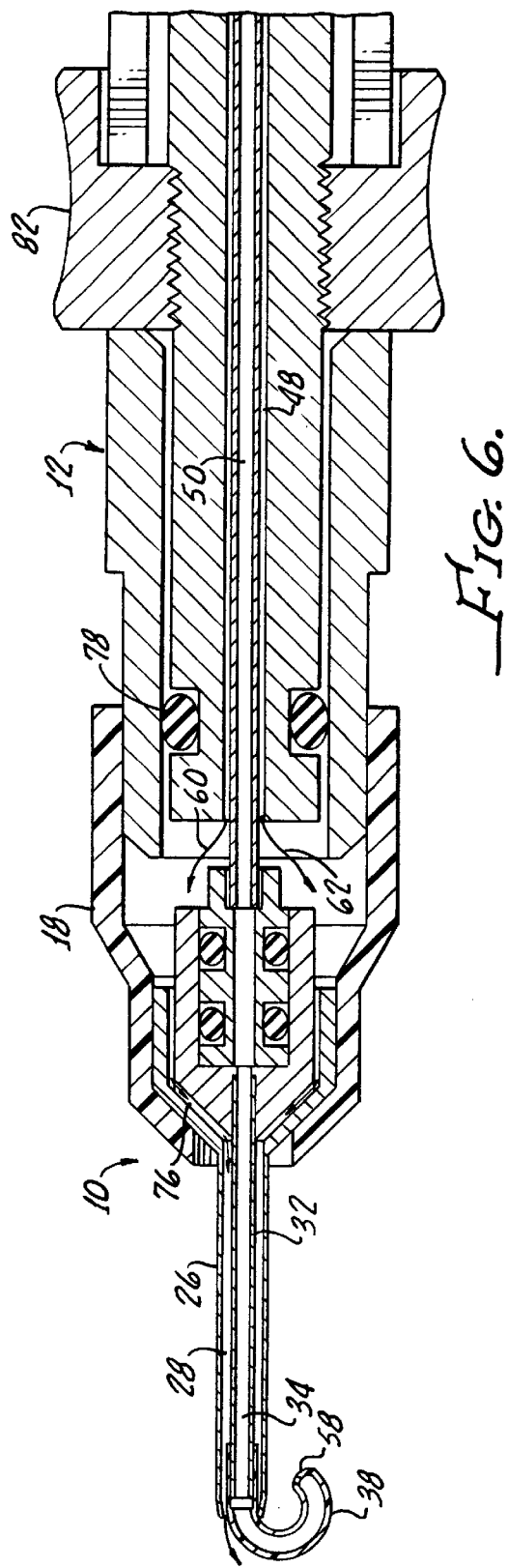

FLEXIBLE IRRIGATION/ASPIRATION TIP ASSEMBLY FOR PROVIDING IRRIGATION TO AN EYE CAPSULE AND FOR ASPIRATING FLUID FROM THE EYE CAPSULE

The present invention generally relates to ophthalmic instruments for disintegrating and removal of tissue and more particularly to an improved handpiece in which the tip assembly is removably attached thereto.

Cataracts are cloudy areas in the eye's lens which occur when certain proteins in the lens form into abnormal clumps. Such clumps gradually enlarge and accordingly interfere with vision by either distorting or blocking the passage of light through the lens.

Cataracts are often age-related, appearing first when a person is in their 40s or 50s, but not affecting vision until after 60. In other situations, cataracts may be related to eye trauma, long-term diabetes, use of steroid medications, or radiation treatments.

In infants, cataracts may be congenital, occurring as a result of infection which may happen during pregnancy, especially toxoplasmosis, cytomegalovirus, syphilis, rubella, or herpes simplex.

Currently, cataracts are the world's leading cause of blindness, accounting for approximately 42% of all cases of blindness throughout the world. In the United States, most cataracts are age-related and affect more than half of all Americans over the age of 65.

Although the exact cause of age-related cataracts is under investigation, many scientists suspect that they are linked to chemical changes affecting a class of eye proteins called crystallins. In general, there is currently no way to prevent age-related cataracts. Although some individuals with cataracts may find their vision improves by using eye glasses, magnifying lenses, or stronger lighting, the only real way to cure cataracts is by surgery.

In that regard, a common medical procedure in eye surgery involves the complete removal of a cataract lens from an eye, which is replaced with an intraocular artificial lens. This procedure is optimized when a very small incision is made in order to minimize patient trauma and unnecessary tissue damage.

Thus, disintegration and removal of damage lens tissue is performed using instruments placed through the small incision.

Phacoemulsification entails using an ultrasonic instrument which utilizes a tubular cutter having a tip which is oscillated by a handpiece along a tip axis at ultrasonic frequencies. Vibration of the tip causes the cortex and lens to disintegrate into particulates which are ready to be aspirated under vacuum through an irrigation/aspiration (I/A) handpiece.

After the cortex is fragmented by phaco handpiece, a safe, manually maneuvered I/A handpiece is used to remove the fragmented tissue. A conventional I/A handpiece has a tip made of metal which is protected by a sleeve. The tip is inserted into the incision and maneuvered by a surgeon throughout a capsular bag surrounding the natural lens. A lumen in the tip is utilized to aspirate the fragmented tissue through a vacuum applied thereto.

Concomitant with aspiration of fluid, irrigation fluid is provided to the eye in order to both maintain the flow of aspirated particles and, importantly, maintain pressure within the eye, specifically the capsular bag, to prevent collapse thereof during the procedure.

Early irrigation/aspiration (I/A) tips were straight, rigid and could not be easily maneuvered within the capsular bag to effectively reach all parts of the cortex to be removed. While such straight tips may be angled slightly from side to side, they cannot be angled sufficiently to allow maneuvering the tip to reach areas at peripheral interior regions of the capsular bag. In order to reach such areas, it is necessary to remove a substantial portion of the anterior capsular wall.

However, it is desirable to limit movement of the instrument at the sclera and the posterior capsule in order to minimize trauma to the eye. Unfortunately, such restricted movement of the instrument within an eye is inconsistent with the object of complete removal of the lens from the capsular bag. Therefore, it should be readily appreciated that certain locations in the eye are relatively inaccessible through the use of a straight, rigid tip.

To overcome this problem, and provide a tip which can access all areas of the capsular bag, I/A tips have been made with bends therein so that the cutting tip may be maneuvered to reach additional parts of the posterior cavity while operating through an incision. These bends are permanent in the needle and may be up to 90° in arc.

However, even with a bent tip, regions at the outer most peripheral portion at the interior of the capsular bag are still not readily accessible to the tip without substantial opening of the incision size at the anterior capsular wall.

Further improvements to I/A tips include a resiliently deformable distal end portion, or tip, which has a curved configuration in its relaxed condition. See U.S. Pat. No. 5,364,405 to Zaleski. This patent is incorporated herewith in its entirety, including specification and drawings, for describing an I/A tip having a resiliently deformable distal end tip portion, otherwise known as a "worm".

The resilient configuration provides for the distal end tip portion of the movably longitudinal sleeve to change not only the amount of silicone tip extending through the sleeve, but to change the length of the arc of the curved tip portion which projects from the sleeve. This permits the curved portion of the tip to operate at various different locations within the eye without having to displace the tip relative to the eye.

This relative movement is between a first position in which the distal portion of the tip is retracted into the distal portion of the sleeve and a second position in which the distal or curved portion of the tip projects outwardly through the sleeve.

While this structure provides for a tip, or worm, which can be maneuvered to remove all the cortex tissue within the capsular bag, the reusability of the worm is limited. This limitation is due to cleaning which requires repeated worm sterilization, as well as constant flexing of the worm as it is repeatedly projected and withdrawn into the sleeve. Previous designs have included a permanent connection between the tip/sleeve and handpiece including the irrigation and aspiration conduits associated therewith. Thus, when the worm resiliency, due to repeated cleaning and flexing, can no longer perform its functions, the entire handpiece must be replaced. Accordingly, the per use cost of such flex Hp I/A handpieces is often prohibitive.

None of the rigid conventional I/A handpiece can support a relative motion between sleeve and aspiration tube, which is the key mechanism of the flex tip I/A handpiece.

In comparison, Phaco handpieces do have relative motion between an aspiration tip and a sleeve. However, in-this case, needle installation requires two steps: First, connection of the needle; and second, installation of the sleeve. This procedure is. reversed when removing the needle.

The hereinabove described needle replacement procedures cannot be utilized with a handpiece having a flexible tip, or worm. This is due to the fact a worm curvature causes it to have a larger extended diameter than the sleeve lumen. Accordingly without a special tool, the worm will not pass through the sleeve. Thus, the two-step installation as described for a phaco handpiece cannot be applied to a handpiece utilizing a worm.

The present invention overcomes this limitation by providing an I/A handpiece which enables a tip assembly to be easily installed onto a handle with alignment between internal couplings of the tip assembly and handle being visually observable and adjustable. Consequently, when the worm tip is no longer serviceable, only the tip assembly needs to be replaced. Accordingly, the flexible tip assembly and handle in accordance with the present invention provides significant economical benefit.

SUMMARY OF THE INVENTION

A flex tip I/A handpiece is provided for the removal of fragmented cortex in an eye capsule (not shown). The handpiece comprises two major subassemblies, namely, a tip assembly and a handle assembly.

A flex worm in the tip assembly provides a means to remove cortex at various angles. The tip assembly, upon connection to the handle assembly provides irrigation fluid to the eye and a means for aspirating fluid and fragmented tissue from the eye.

In general, the tip assembly includes an elongated sleeve which provides a means for protecting an eye capsule wound, through which the sleeve is inserted. The sleeve also enables the passage of irrigation fluid to the eye and the rigidity of sleeve also functions to straighten the worm when needed. The sleeve includes a lumen therethrough along with nipple means for removably coupling the elongate sleeve to a handpiece by elastomeric contact with the handpiece. This elastomeric contact not only provides a seal between the sleeve and the handpiece, but also enables coordinated coupling between the tip assembly and the handpiece to ensure communication therebetween for aspiration and irrigation fluids, as will hereinafter be described in greater detail.

A retractor tube is positioned within the sleeve lumen. This position establishes an irrigation fluid annulus between the sleeve and the tube.

A worm is attached to the retractor tube and the worm/retractor is positioned within the sleeve lumen. Because the worm is flexible, it can be straightened or curved, depending on the relative position of the worm within the sleeve. Since the worm is attached to the retractor, the position of the retractor controls the curvature of worm.

By utilizing the natural tendency of the worm's curvature, the flexible worm will hold the retractor inside of the sleeve/nipple assembly. This is important, because the assembly must be flexible enough for hand maneuvering. Further, the tip assembly must remain intact under the harsh environment of shipping and handling. The tip assembly in accordance with the present invention is thus reliable in ensuring that the worm retractor will not separate or be dislodged from the sleeve/nipple. As hereinabove noted, if the worm/retractor separates from the sleeve, the unit can no longer be field installable.

A retractor and the sleeve are held in an operative relationship with the handpiece by the nipple means. This operative relationship includes not only the transfer of both irrigation and aspiration fluid between the handpiece and the eye capsule, but also the retractile motion of worm.

In that regard, the nipple means is transparent, or translucent, for enabling visual confirmation of the operative coupling relationship between the retractor tube and the handle assembly.

The retractor tube is slidably disposed within the sleeve and the nipple. The flexible worm, attached to the retractor tube, has an arcuate shape with sufficient resiliency to be slidably withdrawn into the distal end of the sleeve. The flexible end portion, or "worm", may be extended from the tube to assume a 180° arc, if desired by an operating physician.

The retractor tube may include socket means disposed at a proximate end thereof for engaging a handle aspiration receiver and establishing aspiration and irrigation fluid communication.

A method in accordance with the present invention provides for removal and coupling a flexible tip assembly to an I/A handle. The method includes providing a handle having an irrigation and aspiration fluid conduits. A tip assembly is provided having an elongated sleeve surrounding a retractor tube for transfer of aspiration of fluid from the eye. The retractor tube is positioned within the sleeve for establishing an irrigation fluid annulus between the sleeve and the retractor tube. Importantly, the method providing for connecting the handle to the tip assembly using a transparent nipple for enabling visual confirmation of proper connection between the handle and the tip assembly.

BRIEF DESCRIPTION OF THE DRAWINGS

The present invention may be more clearly appreciated when taken in conjunction with the accompanying drawings, in which"

FIG. 1 is a perspective view of the flex tip handpiece including an I/A tip assembly and handle in accordance with the present invention, generally showing as part of the tip assembly an elongated sleeve with a transparent nipple for attaching the tip assembly to the handle for enabling visual confirmation of the operative relationship between the tip assembly and the handle;

FIG. 2 is an exploded perspective view of the handpiece shown in FIG. 1, more clearly showing the tip assembly as including a retractor disposed in the sleeve for establishing an irrigation flow annulus between the sleeve and the tube and a worm disposed on a retractor tube for transference of fluid between the eye and the handpiece;

FIGS. 5 and 6 are enlarged views of the tip assembly alone corresponding to the positions set forth in FIGS. 3 and 4, respectively.

DETAILED DESCRIPTION

Figure 3:
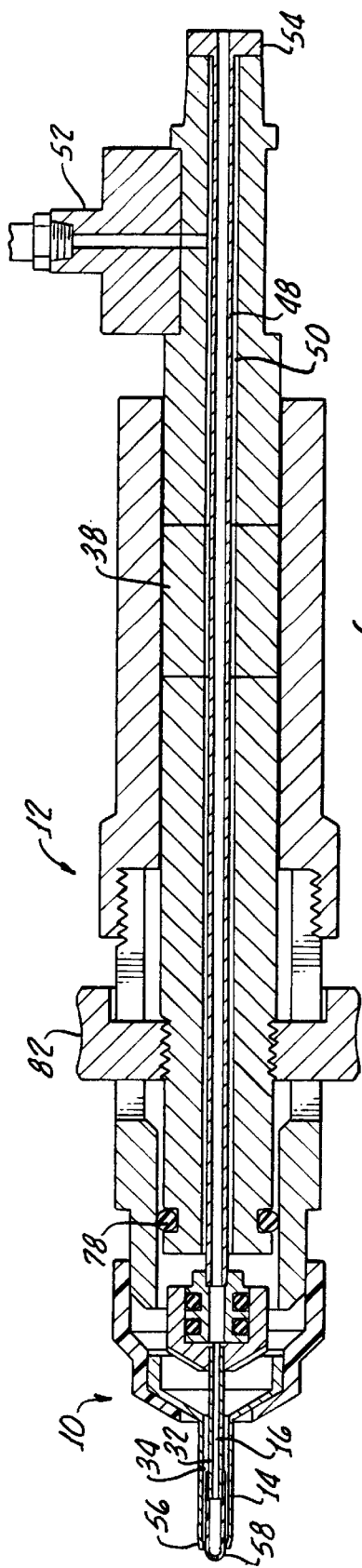
FIG. 3 is a cross-sectional view of the handpiece shown in FIGS. 1 and 2 showing the coupling arrangement between the retractor and handle and a grip for enabling sliding of the worm within the sleeve, the worm being shown withdrawn in FIG. 3.

With reference to FIG. 1, there is shown a flex tip I/A handpiece 8 generally including a tip assembly 10 and handle assembly 12 in accordance with the present invention for providing cortex removal to an eye capsule (not shown). The handle assembly, or handle, 12 provides for connecting fluid conduits and enables a user to hold and manipulate the tip assembly 10 as hereinafter described in greater detail. Irrigation fluid and aspirating fluid communication to and from the eye capsule is provided as will be hereinafter described in greater detail.

With reference to FIG. 2, the tip assembly 10 includes an elongated sleeve 14 having a lumen 16 therethrough. The sleeve provides a means for protecting an eye capsule wound through which the sleeve is inserted and also for containing irrigation fluid.

A nipple 18 provides means for removably coupling the elongated sleeve 14 to the handle 12 by elastomeric contact therewith. The nipple 18 is sized for compression fitting over a collar 22 which receives the nipple. The elastomeric contact provides a seal between the nipple 18 and the collar 22.

The nipple 18 is preferably formed from silicone and importantly the nipple 18 is formed from a translucent or transparent silicone for enabling visual confirmation of an operative relationship between the tip assembly 10 and the handle 12, as will be hereinafter described in greater detail. The elasticity of the silicone enables lateral alignment of the tip and handle assemblies. This is important for enabling proper alignment therebetween.

It should be appreciated that all of the materials of construction in the tip assembly 10 and handle 12 are from conventional materials suitable for use with medical instruments, such as, for example, Titanium.

As most clearly shown in FIG. 2, retractor means 30 includes a tube 32, disposed within the sleeve lumen 16, which establishes an irrigation fluid annulus 34 between the sleeve 14 and the tube 32, the annulus 34 being more easily seen in FIGS. 3–7.

With continued reference to FIG. 2, the retractor means 30 includes a flexible worm 38 installed on the tube 32. The tube 32 includes an enlarged end 40 with a core shaped shoulder 42 and a socket 44 (see FIG. 7) for connection to an aspiration receiver 46. The shoulder 42 helps in holding the alignment of the socket 40 with the receiver 46.

The tube 32 is slidably disposed within the sleeve 14 for transferring disintegrated cortex of the eye capsule to the handle 12 through a coaxial joint of socket 44 and receiver 46, shown in FIGS. 3–7. The handle 12 further includes irrigation fluid and aspiration fluid conduits 48, 50 which are interconnected respectively to an irrigation fluid source (not shown) via a fitting 52 and a vacuum source (not shown) via a fitting 54. The handle 12 design with regard to the conduits 48, 50, and fittings 52, 54 are conventional in nature and may be, according to, for example, U.S. Pat. No. 5,364,405 which is incorporated herewith in its entirety including drawings and specifications for teaching structural aspects of the handle 12 including the conduits 48, 50 and fittings 52, 54. Detailed structural elements and operation of the handpiece are not provided herein, inasmuch as this information is set forth in U.S. Pat. No. 5,364,405.

As hereinabove noted, the retractor means 30 includes the flexible end portion, or worm, 38 having an arcuate shape with sufficient resiliency to be slidably withdrawn into a distal end 56 of the sleeve 14, the worm 38 having a lumen 58 for aspiration of fluid and fragmented tissue into the tip assembly 10 and thereafter through the handle 12 and fitting 54. The structure and operation of the tip assembly with the worm is fully set forth in U.S. Pat. No. 5,364,405, which is incorporated herewith for also teaching the structure and operation of the worm 38.

When the socket 44 (see FIG. 7) is press fitted over the receiver 46, O-rings 70 provide a seal therebetween and at the same time fluid communication is established in the handpiece aspiration conduit 46 and the retractor 30. Also, when the socket 44 and receiver 46 are engaged and the nipple 18 sealably engages the collar 22, a secure irrigation fluid path is established between the handpiece irrigation conduit 48 and the annulus 34 as indicated by the fluid flow arrows 60, 62 in FIG. 6.

Figure 4:
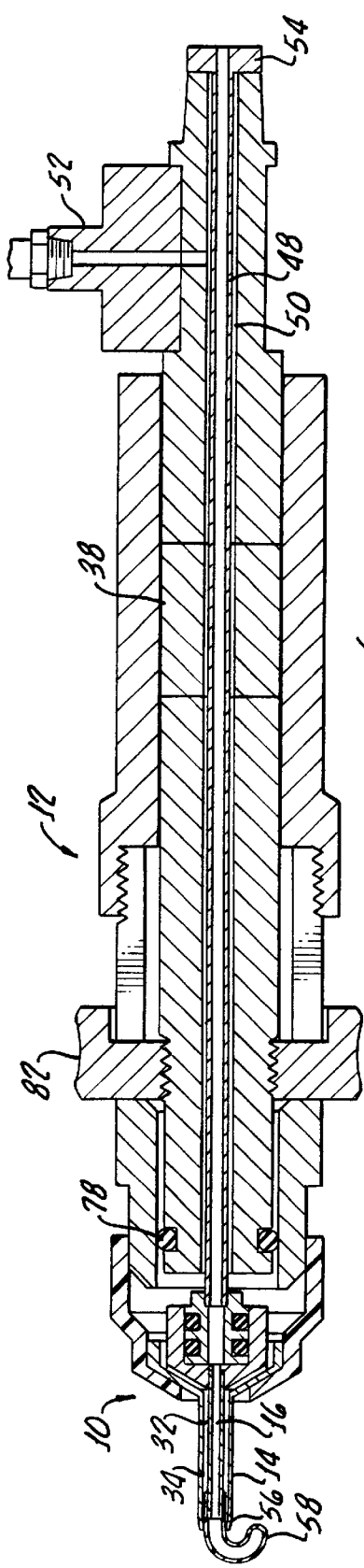
FIG. 4 is a cross section view similar to FIG. 3 showing the retractor in an extended position with a flexible end, or worm, extending in an arcuate fashion from the tube and sleeve.
Figure 7:
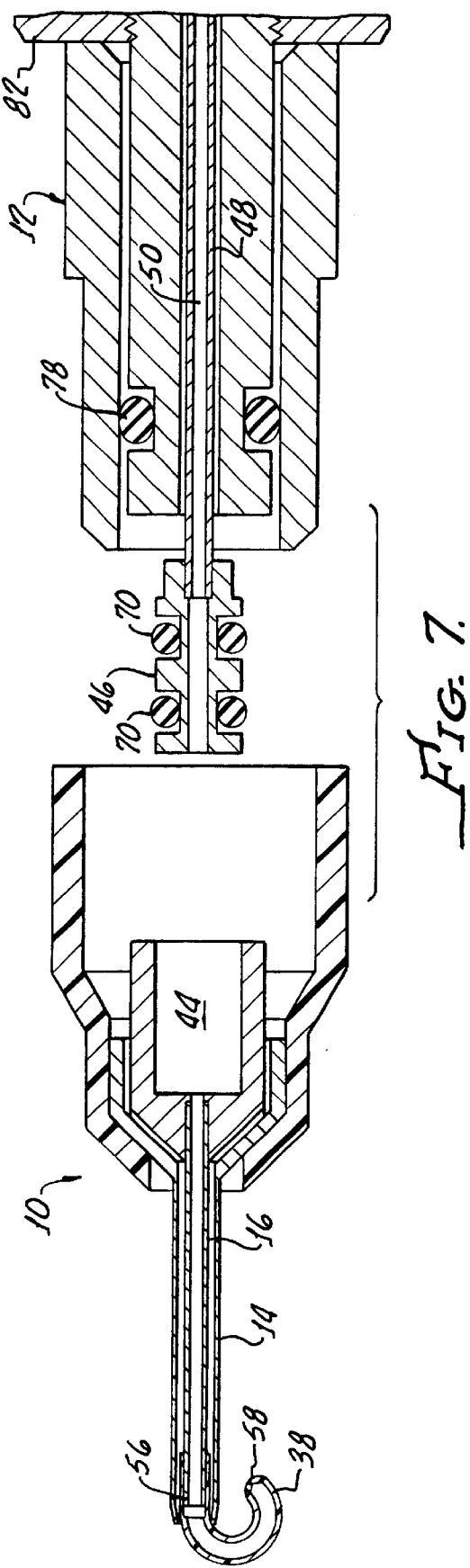
FIG. 7 is an exploded cross section view of the tip assembly and aspiration receiver.

An O-ring 78 enables the retractor 30, and worm, to slide from a retracted position shown in FIGS. 3 and 5 to a fully extended position shown in FIGS. 4 and 6.

This movement is effected through movement of the receiver 46 which is interconnected to a grip 82 and movable within a slot 84, see FIG. 1.

Movement of the grip 82 along the handle assembly 12 will push the flexible end portion of the worm 38 out of the distal end 56 of the sleeve 14.

As hereinabove noted, to complete aspiration path, the tip assembly 10 must be assembled to the handle with the receiver 46 properly engaging the socket 44. Alignment of the receiver and the socket 44 must be made in order to facilitate a proper sealing engagement therebetween. (See FIG. 7).

This is accomplished by the fact that the nipple 18 is transparent, thus enabling the divisional alignment and ensuring proper coupling between the receiver 46 and the socket 44.

Therefore, a method in accordance with the present invention for removably coupling the tip assembly 10 to a handle to assemble an I/A handpiece 8 includes providing a handle 12 having irrigation and aspirating fluid conduits 48, 50 along with a tip assembly 10 having an elongated sleeve 14 and retractor 30 for transferring irrigation fluid and the aspiration fluid at any angle in an eye, and connecting the handle 12 to the tip assembly 10 using a transparent nipple 18 for enabling visual confirmation of proper connection between the handle 12 and the tip assembly 10.

It should be noted that the natural tendency of the worm 38 curvature will hold the retractor 30 inside of the sleeve and nipple 14, 18. Accordingly, assembly 10 is made reliable since the retractor 30 will not slip out of the sleeve 14 and nipple 14, 18. This eliminates what otherwise may create difficulty in field installation.

Although there has been hereinabove described a field replaceable tip assembly and method for a flexible tip I/A handpiece, for the purpose of illustrating the manner in which the invention may be used to advantage, it will be appreciated that the invention is not limited thereto. Accordingly, all modifications, variations, or equivalent arrangements which may occur to those skilled in the art, should be considered to be within the scope of the invention as defined in the appended claims.

What is claimed is:

1. A flexible I/A tip assembly for providing irrigation fluid to an eye capsule and for aspirating fluid from the eye capsule, the tip assembly comprising:

elongated sleeve means for protecting an eye wound through which the sleeve means is inserted and for containing irrigation fluid, the sleeve means including a lumen therethrough;

nipple means for removably coupling said elongated sleeve to a handle, the sleeve and nipple means being formed from an elastomer and the nipple means being removably coupled to the handpiece by elastomeric contact therewith;

retractor means, disposed in the sleeve lumen, for establishing an irrigation fluid annulus between the sleeve means and said retractor means and aspirating fluid from the eye capsule, said sleeve means and retractor means being held in an operative relationship with said handle by said nipple means, for transfer of irrigation fluid and aspirating fluid therebetween, said retractor means being slidably disposed within the sleeve means, said retractor means further comprising a flexible end portion having an arcuate shape with sufficient resiliency to be slidably withdrawn into a distal end of said retractor means; and means defining transparency of said nipple means, for enabling visual confirmation and adjustment of the operative relationship between said retractor means and said handle.

2. The tip assembly according to claim 1 wherein said retractor means comprises socket means, disposed at a proximal end, for engaging a handle aspirating receiver and establishing aspiration and irrigation fluid communication therebetween.

* * * * *